United States Patent [19]

Sloan et al.

[11] 4,412,994

[45] Nov. 1, 1983

[54] MANNICH-BASE HYDROXAMIC ACID PRODRUGS, COMPOSITIONS AND USE

[75] Inventors: Kenneth B. Sloan, Eudora, Kans.; Roy Little, Gainesville, Fla.

[73] Assignee: INTERx Research Corporation, Lawrence, Kans.

[21] Appl. No.: 383,375

[22] Filed: May 28, 1982

Related U.S. Application Data

[63] Continuation of Ser. No. 143,520, Apr. 24, 1980, abandoned.

[51] Int. Cl.³ .................. A61K 31/405; A61K 31/535; C07D 209/18; C07D 413/12
[52] U.S. Cl. ..................... 424/248.53; 424/248.54; 424/250; 424/267; 424/273 P; 424/273 R; 424/274; 424/246; 544/144; 544/373; 544/2; 546/201; 548/300; 548/356; 548/468; 548/500; 260/245.7
[58] Field of Search .................... 544/144, 373, 2; 546/201; 548/300, 356, 468, 500; 260/245.7; 424/248.53, 248.54, 250, 267, 273 R, 273 P, 274, 246

[56] References Cited

PUBLICATIONS

DeMartiis et al., *Chemical Abstracts,* vol. 83 (1975) No. 188384u.

*Primary Examiner*—Robert W. Ramsuer
*Attorney, Agent, or Firm*—T. Y. Cheng; M. A. Monaco; M. C. Sudol, Jr.

[57] ABSTRACT

Novel prodrug forms of known non-steroidal anti-inflammatory agents are disclosed, said prodrugs having the structural formula

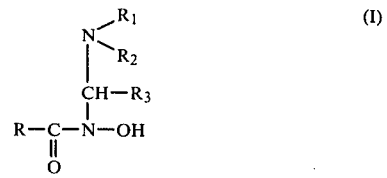

34 Claims, No Drawings

MANNICH-BASE HYDROXAMIC ACID PRODRUGS, COMPOSITIONS AND USE

This is a continuation of application Ser. No. 143,520, filed Apr. 24, 1980, now abandoned.

TECHNICAL FIELD OF THE INVENTION

The present invention relates to novel and useful derivatives of non-steroidal anti-inflammatory drugs containing a carboxylic acid function. In particular, the present invention relates to novel forms of these non-steroidal anti-inflammatory drugs characterized as being (1) more readily bioavailable; (2) less irritating to topical and gastric mucosal membranes; and (3) more permeable through topical membranes such as the ophthalmic membrane, skin, and the like, when administered orally or topically to warm-blooded animals than are the non-steroidal anti-inflammatory drugs from which they are derived.

For the purposes of this specification, the term "prodrug" denotes a derivative of a known and proven prior art non-steroidal anti-inflammatory compound (e.g., indomethacin, sulindac, naproxen, or the like), which derivative, when administered to a warm-blooded animal, "cleaves" in such a manner as to release the proven drug form at its target site or sites of activity. The enzymatic and/or chemical hydrolytic "cleavage" of the compounds of the instant invention occurs in such a manner such that the proven drug form (the conventional non-steroidal anti-inflammatory agent) is released while the remaining "cleaved" moiety remains nontoxic and is metabolized in such a manner that nontoxic-metabolic products are produced.

BACKGROUND OF THE PRIOR ART

Usually, the un-ionized form of a drug is absorbed more efficiently than its ionic species. In the case of non-steroidal anti-inflammatory drugs containing the carboxylic acid functional group such as indomethacin, sulindac, naproxen and the like, the carboxylic acid is significantly ionized at physiological pH. The result is that such non-steroidal anti-inflammatory drugs are poorly absorbed through lipid-water membrane barriers and are irritating. Thus, an object of the present invention is to provide a class of derivatives of non-steroidal anti-inflammatory drugs which would not be significantly ionized at physiological pH and which are reasonably stable, but which hydrolyze readily in vivo and yield upon hydrolysis only the parent non-steroidal anti-inflammatory drug and non-toxic, readily metabolized by-products.

SUMMARY OF THE INVENTION

It is one object of the present invention to provide prodrug forms of conventional non-steroidal anti-inflammatory agents which exhibit oral and topical anti-inflammatory activity when administered to warm-blooded animals and are characterized as being more readily bioavailable, less irritating to topical and gastric mucosal membranes and more permeable through topical membranes, e.g., ophthalmic membrane or skin, than are the non-steroidal anti-inflammatory drugs from which they are derived.

It is another object of the present invention to provide such prodrug forms of conventional anti-inflammatory compounds which, following administration, will "cleave" in such a manner as to enable the original parent moiety (indomethacin, sulindac, naproxen, or other known non-steroidal anti-inflammatory agent) to be released at its therapeutic site or sites of anti-inflammatory activity and to further permit the cleaved moiety(ies) unassociated with the parent moiety to be metabolized in a nontoxic fashion.

The foregoing objects are achieved by topically or orally administering to a warm-blooded animal afflicted with inflammation, a therapeutically effective anti-inflammatory amount of a compound having the formula:

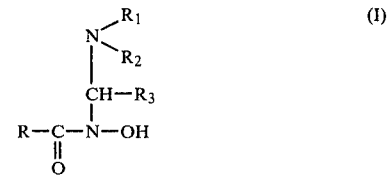

wherein

is the acyl residue of any non-steroidal anti-inflammatory agent containing a carboxylic acid function; $R_1$ and $R_2$, which can be the same or different, each represent a member selected from the group consisting of alkyl of 1 to 20 carbon atoms; alkenyl of 2 to 20 carbon atoms; aryl of 6 to 10 carbon atoms; cycloalkyl of 3 to 8 carbon atoms; cycloalkenyl of 4 to 8 carbon atoms; alkynyl of 2 to 20 carbon atoms; aralkyl, alkaryl, aralkenyl, aralkynyl, alkenylaryl, and alkynylaryl, wherein the alkyl, alkenyl, alkynyl, and aryl portions are defined as above; and substituted derivatives of the above-defined alkyl, alkenyl, aryl, cycloalkyl, cycloalkenyl, alkynyl, aralkyl, alkaryl, aralkenyl, aralkynyl, alkenylaryl and alkynylaryl radicals, said derivatives having one or more substituents each of which are selected from the group consisting of $C_1$–$C_8$ alkyl, $C_1$–$C_8$ alkoxy, $C_1$–$C_8$ alkanoyl, $C_1$–$C_8$ alkanoyloxy, halo, $C_1$–$C_8$ haloalkyl, cyano, $C_2$–$C_9$ carbalkoxy, $C_1$–$C_8$ alkylthio, nitro, $C_1$–$C_8$ haloalkyl having 1 or more halo substituents, dialkylamino wherein the alkyl portions each contain 1 to 8 carbon atoms, carboxy, dialkylcarbamyl wherein the alkyl portions each contain 1 to 3 carbon atoms, and $C_1$–$C_8$ alkylsulfonyl; or $R_1$ or $R_2$ are combined so that —$NR_1R_2$ together represent the residue of a saturated or unsaturated heterocyclic compound containing one secondary nitrogen atom; $R_3$ is selected from the group consisting of hydrogen, $R_1'$,

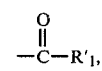

—$CH_2OCOR_1'$, —$CH_2ONO_2$, pyridyl, furyl, cyano, carbamyl, $C_2$–$C_9$ alkylcarbamyl and dialkylcarbamyl wherein the alkyl portions each contain 1 to 8 carbon atoms; $R_1'$ is any radical encompassed by the definition of $R_1$ above; or a nontoxic pharmaceutically acceptable acid addition salt or oxide thereof.

The term "nontoxic pharmaceutically acceptable acid addition salt" as used herein generally includes the nontoxic acid addition salts of selected compounds of formula (I), formed with nontoxic inorganic or organic acids. For example, the salts include those derived from inorganic acids such as hydrochloric, hydrobromic, sulfuric, sulfamic, phosphoric, nitric and the like; and the salts prepared from organic acids such as acetic, propionic, succinic, glycollic, stearic, lactic, malic, tartaric, citric, ascorbic, pamoic, maleic, hydroxymaleic, phenylacetic, glutamic, benzoic, salicylic sulfanilic, fumaric, methanesulfonic, toluenesulfonic, and the like.

The term "oxide" as used herein includes the non-toxic pharmaceutically acceptable oxides of selected compounds of formula (I). Usually, the oxides are N-oxides but they may be sulfoxides in the event that —$NR_1R_2$ represents the residue of a sulfur-containing heterocycle. The oxides are prepared by oxidation of the selected compounds of formula (I) with a suitable oxidizing agent, e.g. m-chloroperbenzoic acid or hydrogen peroxide, in an appropriate inert solvent such as dichloromethane, benzene or chloroform.

The term "acyl residue" as used herein with respect to any non-steroidal anti-inflammatory agent containing a carboxylic acid function is intended to represent that portion of the anti-inflammatory compound which remains after removal of the —OH from the —COOH portion of the molecule.

The chemical structure of the non-steroidal anti-inflammatory drugs whose acyl residues are encompassed by formula (I) is not critical, so long as those drugs contain a carboxylic acid function. Suitable anti-inflammatory agents from which the instant prodrugs are derived include, but are not limited to, indomethacin, aspirin, naproxen, fenoprofen, sulindac, ibuprofen, tolmetin, difunisal, flurbiprofen, indoprofen, mefanamic acid, fenclozic acid, ketoprofen, alcolfenac, bucloxic acid, meclofenamic acid, flufenamic acid, cinchophen, voltaren, cinmetacin, lbufenac, furobufen, fenclofenac, prodolic acid, pirprofen, oxoprozin, clonixin, fluprofen and flutiazin.

With respect to the radicals encompassed by $R_1$, $R_2$ and —$NR_1R_2$ in formula (I) and throughout this specification, the following definitions are applicable:

The expression "the residue of a saturated or unsaturated heterocyclic compound containing one secondary nitrogen atom" as used herein is intended to indicate the portion of the heterocyclic compound which remains after removal of the hydrogen atom from the secondary nitrogen. Thus, the term "saturated or unsaturated heterocyclic compound containing one secondary nitrogen atom" encompasses saturated monocycles containing one or more hetero atoms in the ring, optionally bearing one or more substituents such as phenyl, benzyl and methyl; and unsaturated one and two ring systems containing one or more double bonds and one or more ring hetero atoms, optionally substituted with one or more methyl groups. In every case, the substituents and double bonds, if any, must be located such that the parent heterocyclic compound from which the residue —$NR_1R_2$ is derived is a compound of the formula $HNR_1R_2$, i.e., the parent compound invariably contains one N which is a secondary nitrogen atom. When the parent heterocycle contains more than one nitrogen atom, one nitrogen must be a secondary nitrogen and any other nitrogen must be tertiary. In any case, the parent compound can contain other hetero atoms, e.g. sulfur and/or oxygen. Illustrative of residues of saturated monocyclic heterocyclics which are encompassed by the —$NR_1R_2$ term are morpholino, perhydro-1,2,4-oxathiazin-4-yl, 1-pyrrolidinyl, 4-benzyl-1-piperazinyl, 4-methyl-1-piperazinyl, piperidino, hexamethyleneimino, 4-phenylpiperidino, 2-methyl-1-pyrazolidinyl, 3-methyl-1-imidazolidinyl, 4-benzylpiperidino and 4-phenyl-1-piperazinyl. Exemplary of residues of unsaturated one and two ring heterocyclic systems represented by —$NR_1R_2$ are radicals such as 1-imidazolyl, 1-pyrrolyl, 1-pyrazolyl, 1-indolinyl, 2-isoindolinyl, 1-indolyl, 2-isoindolyl, 1H-indazol-1-yl, and 7-purinyl; and radicals derived from compounds such as pyrazoline, pyrroline and imidazoline wherein there is one secondary nitrogen atom, e.g., radicals of the type

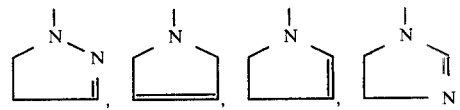

and the like. In addition, any of the aforesaid unsaturated one and two ring heterocycles can be optionally substituted with one or more methyl groups.

The term "aryl" as used herein can be exemplified by phenyl and naphthyl.

In addition, here and throughout this specification, the following examples are applicable: The alkyl radicals include methyl, ethyl, propyl, butyl, pentyl, hexyl, heptyl and octyl and the branched-chain isomers thereof, as well as their straight and branched-chain higher homologues in the instances where "alkyl" can contain more than 8 carbon atoms. The alkenyl and alkynyl radicals may be straight or branched-chain, for example, vinyl, propenyl, butenyl, ethynyl, propynyl, butynyl, and the like. The cycloalkyl and cycloalkenyl radicals are exemplified by cyclopentyl, cyclohexyl and cyclopentenyl. The aralkyl, aralkenyl and aralkynyl radicals are of the type -alkylene-aryl, -alkenylene-aryl and -alkynylene-aryl, wherein aryl is as defined above and the alkylene, alkenylene and alkynylene moieties contain up to 20 carbon atoms (preferably up to 6 carbon atoms) and can be straight or branched-chain. The alkylene moieties are typified by methylene, ethylene, propylene, trimethylene, 1,2-butylene, 2,3-butylene, tetramethylene and the like. Exemplary of the contemplated alkenylene and alkynylene moieties are vinylene, ethynylene, butenylene and butynylene. Additionally, the alkoxy, alkanoyl, alkanoyloxy, carbalkoxy, alkylthio, dialkylamino, dialkylcarbamyl, alkylsulfonyl and alkylcarbamyl radicals are of the type

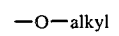

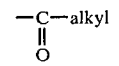

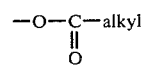

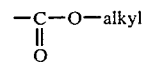

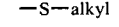

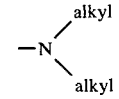

-continued

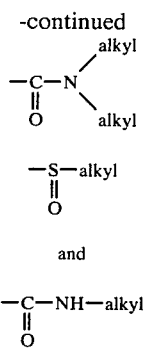

respectively, wherein the alkyl group in each instance contains 1 to 8 carbon atoms.

DETAILED DESCRIPTION OF THE INVENTION

While all of the compounds encompassed by formula (I) above essentially satisfy the objectives of the present invention, the following selected compounds are preferred:

1. α-[1-(4'-Chlorobenzoyl)-5-methoxy-2-methylindol-3-yl]-N-(morpholinomethyl)acetohydroxamic acid.
2. α-[1-(4'-Chlorobenzoyl)-5-methoxy-2-methylindol-3-yl]-N-(N',N'-diethylaminomethyl)acetohydroxamic acid.
3. α-[1-(4'-Chlorobenzoyl)-5-methoxy-2-methylindol-3-yl]-N-[(4-methylpiperazin-1-yl)methyl]acetohydroxamic acid.
4. α-[1-(4'-Chlorobenzoyl)-5-methoxy-2-methylindol-3-yl]-N-(piperidinomethyl)acetohydroxamic acid.
5. α-[1-(4'-Chlorobenzoyl)-5-methoxy-2-methylindol-3-yl]-N-[(pyrrolidin-1-yl)methyl]acetohydroxamic acid.
6. α-[1-(4'-Chlorobenzoyl)-5-methoxy-2-methylindol-3-yl]-N-(N',N'-dicyclohexylaminomethyl)acetohydroxamic acid.
7. α-[1-(4'-Chlorobenzoyl)-5-methoxy-2-methylindol-3-yl]-N-[(pyrrol-1-yl)methyl]acetohydroxamic acid.
8. α-[1-(4'-Chlorobenzoyl)-5-methoxy-2-methylindol-3-yl]-N-[(indol-1-yl)methyl]acetohydroxamic acid.
9. α-[1-(4'-Chlorobenzoyl)-5-methoxy-2-methylindol-3-yl]-N-[(isoindol-2-yl)methyl]acetohydroxamic acid.
10. α-[1-(4'-Chlorobenzoyl)-5-methoxy-2-methylindol-3-yl]-N-[(purin-7-yl)methyl]acetohydroxamic acid.
11. α-[1-(4'-Chlorobenzoyl)-5-methoxy-2-methylindol-3-yl]-N-(N',N'-dimethylaminomethyl)acetohydroxamic acid.
12. α-[1-(4'-Chlorobenzoyl)-5-methoxy-2-methylindol-3-yl]-N-(N',N'-diisopropylaminomethyl)acetohydroxamic acid.
13. α-[1-(4'-Chlorobenzoyl)-5-methoxy-2-methylindol-3-yl]-N-(N',N'-dipentylaminomethyl)acetohydroxamic acid.
14. α-[1-(4'-Chlorobenzoyl)-5-methoxy-2-methylindol-3-yl]-N-(N',N'-dioctylaminomethyl)acetohydroxamic acid.
15. α-{cis-5-Fluoro-2-methyl-1-[4'-(methylsulfinyl)benzylidene]inden-3-yl}-N-(piperidinomethyl)acetohydroxamic acid.
16. α-{cis-5-Fluoro-2-methyl-1-[4'-(methylsulfinyl)benzylidene]inden-3-yl}-N-[(N'-benzyl-N'-phenyl)aminomethyl]-acetohydroxamic acid.
17. α-{cis-5-Fluoro-2-methyl-1-[4'-(methylsulfinyl)benzylidene]inden-3-yl}-N-(morpholinomethyl)acetohydroxamic acid.
18. α-{cis-5-Fluoro-2-methyl-1-[4'-(methylsulfinyl)benzylidene]inden-3-yl}-N-[(imidazol-1-yl)methyl]acetohydroxamic acid.
19. α-(6-Methoxynaphthalen-2-yl)-α-methyl-N-(N',N'-diethylaminomethyl)acetohydroxamic acid.
20. α-Methyl-α-(3-phenoxy)phenyl-N-(piperidinomethyl)-acetohydroxamic acid.
21. α-Methyl-α-(3-phenoxy)phenyl-N-[(N'-benzyl-N'-phenyl)aminomethyl]acetohydroxamic acid.
22. α-Methyl-α-(3-phenoxy)phenyl-N-(morpholinomethyl)-acetohydroxamic acid.
23. α-Methyl-α-(3-phenoxy)phenyl-N-[(imidazol-1-yl)methyl]acetohydroxamic acid.
24. α-Methyl-α-[4-(2'-methylpropyl)]phenyl-N-(morpholinomethyl)acetohydroxamic acid.
25. α-Methyl-α-[4-(2'-methylpropyl)]phenyl-N-(piperidinomethyl)acetohydroxamic acid.
26. α-[1-Methyl-5-(p-toluoyl)pyrrol-2-yl]-N-(N',N'-diethylaminomethyl)acetohydroxamic acid.
27. α-Methyl-α-[4-(1'-oxoisoindol-2'-yl)]phenyl-N-(piperidinomethyl)acetohydroxamic acid.
28. α-Methyl-α-[4-(1'-oxoisoindol-2'-yl)]phenyl-N-(morpholinomethyl)acetohydroxamic acid.

It will be apparent to those skilled in the art that the preferred compounds listed above are derived from indomethacin, sulindac, naproxen, fenoprofen, ibuprofen, tolmetin and indoprofen. Other suitable anti-inflammatory agents from which the instant prodrugs can be derived include, but are not limited to, fenclozic acid, ketoprofen, alcofenac, bucloxic acid, meclofenamic acid, flufenamic acid, cinchophen, voltaren, cinmetacin, ibufenac, furobufen, fenclofenac, prodolic acid, pirpofen, oxoprozin, clonixin, fluprofen, flutiazin, aspirin, diflunisal, flurbiprofen and mefenamic acid.

The novel prodrugs of formula (I) can be prepared by first reacting the acid chloride of a non-steroidal anti-inflammatory agent of the formula

wherein

is as hereinbefore defined, with hydroxylamine, suitably employed in the form of its hydrochloride H$_2$NOH.HCl. The reaction is conveniently conducted in the presence of a suitable base, e.g., potassium carbonate, in an appropriate organic solvent or mixture of solvents, e.g., diethyl ether/tetrahydrofuran. The resultant intermediate is of the formula

wherein

is as hereinbefore defined. The hydroxamic acid of formula (III) is then reacted with formaldehyde or other aldehyde of the type R₃CHO wherein R₃ is as defined above, and a secondary amine of the formula

wherein R₁, R₂ and —NR₁R₂ are defined as before, to afford the desired prodrug of formula (I). The reaction is carried out in an appropriate organic solvent such as tetrahydrofuran, and the formaldehyde can be conveniently introduced into the reaction mixture in the form of formalin (a solution of about 37% by weight of formaldehyde gas in water, usually with 10–15% methanol added to prevent polymerisation).

The acid chloride starting material of formula (II) above is prepared in known manner from the corresponding non-steroidal anti-inflammatory agent

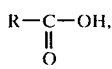

wherein

is defined as above, typically by treatment of that acid with thionyl chloride.

Without further elaboration, it is believed that one of ordinary skill in the art can, using the preceding description, utilize the present invention to its fullest extent. Therefore, the following preferred embodiments are to be construed as merely illustrative and not limitative of the remainder of the specification and claims in any way whatsoever.

EXAMPLE 1

The Preparation of the Acid Chloride of 1-(4′-Chlorobenzoyl)-5-methoxy-2-methyl-3-indolylacetic Acid, i.e., Indomethacin Acid Chloride To 9.00 g (0.0757 mol) of thionyl chloride in 400 ml of dichloromethane were added 5.55 g (0.076 mol) of dimethylformamide in 100 ml of dichloromethane. After 10 minutes at room temperature, the above solution was allowed to react with a dichloromethane (100 ml) suspension containing 25.7 g (0.072 mol) of indomethacin. The resulting faintly orange solution was immediately concentrated in vacuo to give a light yellow residue which was triturated with 500 ml of ether overnight. The precipitate was then removed by filtration and dried to give 16.7 g (mp 124°–126° C., 61% yield) of the desired indomethacin acid chloride: IR (KBr) 1790 and 1675 cm⁻¹ (s) (C=O); NMR (CDCl₃) δ7.60 (AB quartet, 4, J=9 Hz, $\Delta_{v_{AB}}$=11 Hz, aromatic H̲), 7.0–6.55 (m, 3, aromatic H), 4.17 (s, 2, C̲H₂COCl) 3.83 (s, 3, O—CH₃) and 2.41 (s, 3, CH₃—C=C).

Anal. Calcd for C₁₉H₁₅Cl₂NO₃: C, 60.65; H, 4.02; N, 3.72. Found: C, 60.59; H, 4.08; N, 3.50.

EXAMPLE 2

The Preparation of α-[1-(4′-Chlorobenzoyl)-5-methoxy-2-methylindol-3-yl]acetohydroxamic Acid, i.e., Indomethacin Hydroxamic Acid Hydroxylamine hydrochloride (7.47 g, 0.107 mole) and potassium carbonate (14.84 g, 0.107 mole) were dissolved in 20 ml of H₂O. 1000 ml of ethyl ether were added and the resulting suspension was stirred for 10 minutes. Then, a suspension of indomethacin acid chloride (40.46 g, 0.107 mole) in 600 ml of tetrahydrofuran was added and the reaction mixture was stirred overnight. The suspension was then filtered and the residue was washed twice with ethyl ether, then was suspended in 600 ml of boiling tetrahydrofuran and filtered while hot. The filtrate was concentrated to 150 ml and allowed to crystallize at room temperature overnight. The crystals were removed by filtration and washed twice with ethyl ether to give 18.72 g (mp 147°–150° C., 47% yield) of slightly yellow fibrous crystals which were shown to be the pure product: NMR (DMSO-d₆) δ10.65 (s, 1, NOH̲), 8.8 (bm, 1, —NH̲OH), 7.67 (s, 4, —C₆H̲₄Cl), 7.22–6.6 (m, 3, —C₆H̲₃OCH₃), 3.80 (s, 3, —OCH̲₃), 3.42 (s, 2, O=CCH̲₂—), 2.28 (s, 3, CCH̲₃), IR (KBr) 3300–3150 cm⁻¹ (b) (NO—H), 1650, 1630 cm⁻¹ (N—C=O).

Anal. Calcd for C₁₉H₁₇ClN₂O₄: C, 61.21; H, 4.60; N, 7.52. Found: C, 61.32; H, 4.80; N, 7.00.

Similarly prepared from their acid chlorides are the hydroxamic acid derivatives of sulindac, naproxen, fenoprofen, ibuprofen, tolmetin and indoprofen. The corresponding hydroxamic acid derivatives of the other anti-inflammatory agents specified herein can be prepared in like manner.

EXAMPLE 3

The Preparation of α-[1-(4′-Chlorobenzoyl)-5-methoxy-2-methylindol-3-yl]-N-(morpholinomethyl)acetohydroxamic Acid Formalin (0.82 g) was mixed with morpholin (0.71 g, 0.0082 mole) in 90 ml of tetrahydrofuran, then indomethacin hydroxamic acid (3.04 g, 0.0082 mole) was added. The resulting suspension was heated in a hot water bath until all the solids had dissolved, then the reaction vessel was stoppered and the solution was allowed to cool overnight. During that time, a small amount of crystals formed. The solution was diluted to 250 ml with cyclohexane and allowed to stand for 2 hours. The crystals which formed were removed by filtration and washed twice with cyclohexane, then dried in vacuo (60° C. for 8 hours) to give 2.01 g (mp 179°–180° C., 68% yield) of white powder which was pure product: NMR (DMSO-d₆) δ7.70 (s, 4, —C₆H̲₄Cl), 7.10–6.70 (m, 3, —OC₆H̲₃), 4.35 (s, 2, NCH̲₂N), 3.84 (s, 2, —COCH̲₂—), 3.77 (s, 3, —OCH̲₃), 3.26 (m, 4, O(CH̲₂)₂—), ~2.6 (m, 4, N(CH̲₂)₂—), 2.24 (s, 3, C—CH̲₃); IR (KBr), 3150 cm⁻¹ (bw) (—NO—H), 2900 cm⁻¹ (C—H), 1660 cm⁻¹ (s) (NC=O), 1600 cm⁻¹ (s) (HONC=O).

Anal. Calcd for C₂₄H₂₅ClN₃O₅: C, 61.21; H, 5.35; N, 8.92. Found: C, 61.44; H, 5.68; N, 8.50.

EXAMPLE 4

The preparation of
α-[1-(4'-Chlorobenzoyl)-5-methoxy-2-methylindol-3-yl]-N-[(4-methylpiperazin-1-yl)methyl]acetohydroxamic Acid This preparation was carried out analogously to the procedure of Example 3 above, using 3.31 g (0.0089 mole) of indomethacin hydroxamic acid, 0.89 g of formalin and 0.89 g (0.0089 mole) of N-methylpiperazine in 90 ml of tetrahydrofuran. Crystallization of the product was accomplished by concentrating the reaction solution to 30 ml and then diluting that solution to 100 ml with cyclohexane. The resultant cloudy solution was allowed to crystallize over 3 days' time, then the crystals were removed by filtration and washed twice with a mixture of hexanes to give 3.53 g (82% yield, mp 143°–145° C.) of off-white, powdery crystalline product: NMR (DMSO-$d_6$) δ7.66 (s, 4, —$C_6H_4Cl$), 7.10–6.60 (m, 3, —$OC_6H_3$—), 4.33 (s, 2, —$NCH_2N$), 3.48 (s, 2, $COCH_2$—), 3.41 (s, 3, —$OCH_3$), 2.7–2.0 (m, 8, —$N(CH_2CH_2)_2N$—), 2.19 (s, 3, $NCH_3$), 2.16 (s, 3, C—$CH_3$); IR (KBr), 2800–3000 $cm^{-1}$ (m) (C-H), 1665 $cm^{-1}$ (s) (NC=O), 1600 $cm^{-1}$ (s) (HONC=O).

Anal. Calcd for $C_{25}H_{29}ClN_4O_4$: C, 61.91; H, 6.03; N, 11.56. Found: C, 62.07; H, 6.00; N, 11.21.

EXAMPLE 5

The Preparation of
α-[1-(4'-Chlorobenzoyl)-5-methoxy-2-methylindol-3-yl]-N-(N', N'-diethylaminomethyl)acetohydroxamic Acid This preparation and crystallization were carried out analogously to the procedures of Examples 3 and 4 above, using 3.15 g (0.0085 mole) of indomethacin hydroxamic acid, 0.85 g of formalin and 0.62 (0.0085 mole) of diethylamine in 70 ml of tetrahydrofuran. After 3 days of crystallizing, the crystalline product was removed by filtration and washed twice with a mixture of hexanes to give 3.08 g (79% yield, mp 134°–137° C.) of white powder: NMR (CDCl$_3$) δ8.03 (bs, 1, NOH), 7.7–6.7 (m, 7, aromatic-H), 4.42 (s, 2, $NCH_2N$), 3.85 (s, 2, —$COCH_2$), 3.82 (s, 3, —$OCH_3$), 2.65 (q, 4, J=8 Hz, $NCH_2$), 2.35 (s, 3, C—$CH_3$), 1.04 (t, 6, J=8 Hz, $NCH_2CH_3$); IR (KBr) 3150 $cm^{-1}$ (w) (NO—H), 2800-3000 $cm^{-1}$ (w) (C-H), 1667 $cm^{-1}$ (s) (NC=O), 1600 $cm^{-1}$ (s) (HONC=O).

Anal. Calcd for $C_{24}H_{28}ClN_3O_4$: C, 62.94; H, 6.16; H, 9.18. Found: C, 62.51; H, 6.18; N, 8.90.

In similar fashion, the other compounds of the present invention can be prepared with similar success by merely following the preceding examples and substituting the appropriate generically and/or specifically described reactants and/or operating conditions of this invention for those of the preceding examples. Thus, the following additional compounds can be prepared by following the above reaction scheme:

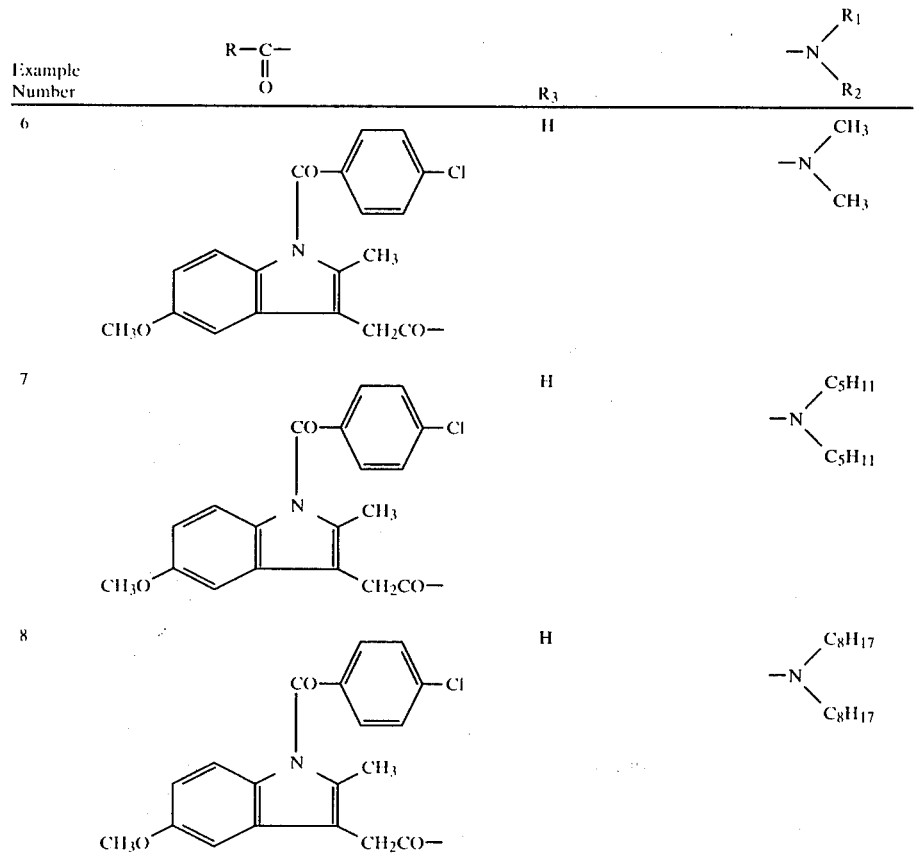

-continued
COMPOUNDS OF FORMULA (I)
| Example Number | R—C(=O)— | R₃ | —N(R₁)(R₂) |
|---|---|---|---|
| 9 | 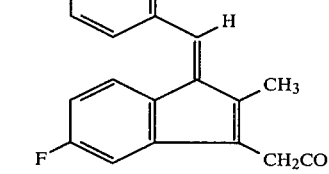 | H | 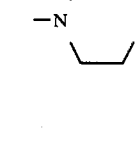 |
| 10 | 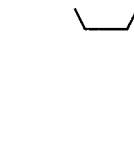 | H | 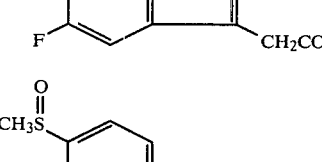 |
| 11 | 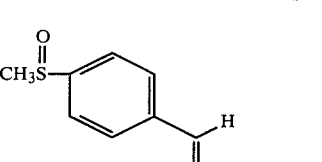 | H | 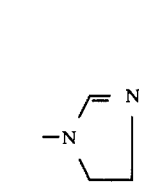 |
| 12 | 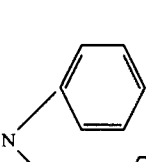 | H | 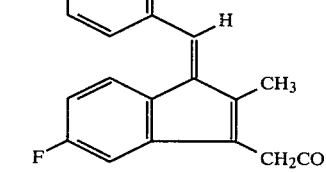 |
| 13 | 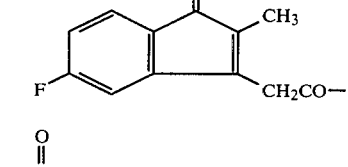 | H |  |
| 14 | 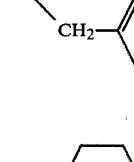 | H | 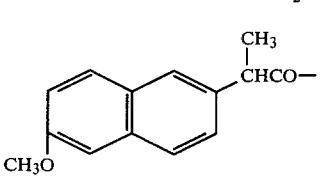 |
| 15 | 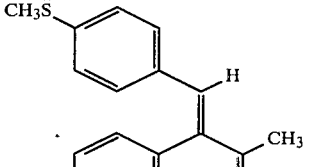 | H | 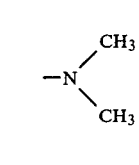 |

-continued

COMPOUNDS OF FORMULA (I)

| Example Number | R—CO— | R$_3$ | —N(R$_1$)(R$_2$) |
|---|---|---|---|
| 16 | 3-phenoxyphenyl-CH(CH$_3$)-CO— | H | piperidino |
| 17 | 3-phenoxyphenyl-CH(CH$_3$)-CO— | H | morpholino |
| 18 | 2-(CH$_3$COO)-C$_6$H$_4$-CO— | H | —N(CH$_3$)$_2$ |
| 19 | 2-(CH$_3$COO)-C$_6$H$_4$-CO— | H | —N(C$_5$H$_{11}$)$_2$ |
| 20 | (CH$_3$)$_2$CHCH$_2$-C$_6$H$_4$-CH(CH$_3$)-CO— | H | piperidino |
| 21 | (CH$_3$)$_2$CHCH$_2$-C$_6$H$_4$-CH(CH$_3$)-CO— | H | —N(C$_6$H$_5$)(CH$_2$C$_6$H$_5$) |
| 22 | (CH$_3$)$_2$CHCH$_2$-C$_6$H$_4$-CH(CH$_3$)-CO— | H | morpholino |
| 23 | (CH$_3$)$_2$CHCH$_2$-C$_6$H$_4$-CH(CH$_3$)-CO— | H | imidazol-1-yl |
| 24 | 1-methyl-5-(4-methylbenzoyl)-pyrrol-2-yl-CH$_2$CO— | H | —N(CH$_3$)$_2$ |
| 25 | 1-methyl-5-(4-methylbenzoyl)-pyrrol-2-yl-CH$_2$CO— | H | —N(C$_2$H$_5$)$_2$ |

-continued

COMPOUNDS OF FORMULA (I)

| Example Number | R—C(=O)— | $R_3$ | —N(R_1)(R_2) |
|---|---|---|---|
| 26 | 2,4-difluoro-biphenyl with CO— and OH (4-hydroxy-2',4'-difluorobiphenyl-3-carbonyl) | H | piperidin-1-yl |
| 27 | 4-hydroxy-2',4'-difluorobiphenyl-3-carbonyl | H | —N(phenyl)(CH$_2$-phenyl) |
| 28 | 4-hydroxy-2',4'-difluorobiphenyl-3-carbonyl | H | morpholin-4-yl |
| 29 | 4-hydroxy-2',4'-difluorobiphenyl-3-carbonyl | H | imidazol-1-yl |
| 30 | 2-fluorobiphenyl-4-yl-CH(CH$_3$)CO— | H | —N(CH$_3$)$_2$ |
| 31 | 2-fluorobiphenyl-4-yl-CH(CH$_3$)CO— | H | —N(C$_2$H$_5$)$_2$ |
| 32 | 2-fluorobiphenyl-4-yl-CH(CH$_3$)CO— | H | —N(C$_5$H$_{11}$)$_2$ |
| 33 | 2-(1-oxoisoindolin-2-yl)phenyl-CH(CH$_3$)CO— | H | piperidin-1-yl |

-continued
COMPOUNDS OF FORMULA (I)

| Example Number | R—C(=O)— | R₃ | —N(R₁)(R₂) |
|---|---|---|---|
| 34 | 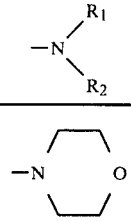 2-(benzyl-N-phenyl)-benzamide with CH₃CHCO— on phenyl | H | morpholino (—N(CH₂CH₂)₂O) |
| 35 | 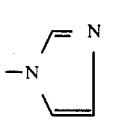 same as 34 | H | imidazol-1-yl |
| 36 | 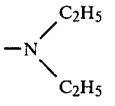 2-(2,3-dimethylphenylamino)benzoyl (CO—) | H | —N(C₂H₅)₂ |
| 37 | 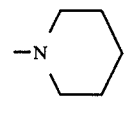 2-(4-chlorophenyl)-4-thiazolyl-CH₂CO— | H | piperidin-1-yl |
| 38 | 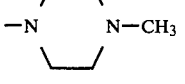 3-benzoyl-α-methylphenylacetyl (CH₃CHCO—) | H | 4-methylpiperazin-1-yl (—N(CH₂CH₂)₂N—CH₃) |
| 39 | 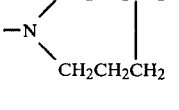 3-chloro-4-allyloxyphenylacetyl (CH₂=CHCH₂O—, Cl, CH₂CO—) | H | 2-methylpyrrolidin-1-yl (—N(CH₂CH₂CH₂)(CH₂CH₂) with CH₃) |
| 40 | 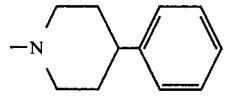 2-chloro-6-cyclohexylphenyl-COCH₂CH₂CO— | H | 4-phenylpiperidin-1-yl |
| 41 | 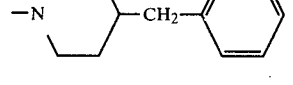 2-(2,6-dichloro-3-trifluoromethylphenylamino)benzoyl | H | 4-benzylpiperidin-1-yl (—N⟨⟩CH₂—C₆H₅) |

-continued

COMPOUNDS OF FORMULA (I)

| Example Number | R—CO— | $R_3$ | $-N\begin{smallmatrix}R_1\\R_2\end{smallmatrix}$ |
|---|---|---|---|
| 42 | 2-[(3-trifluoromethylphenyl)amino]benzoyl— | H | 4-phenylpiperazin-1-yl |
| 43 | 2-phenylquinoline-4-carbonyl— | H | pyrazol-1-yl |
| 44 | [2-(2,6-dichlorophenylamino)phenyl]CH$_2$CO— | H | —N(C$_2$H$_5$)$_2$ |
| 45 | [1-cinnamoyl-2-methyl-5-methoxyindol-3-yl]CH$_2$CO— | H | piperidin-1-yl |
| 46 | (CH$_3$)$_2$CHCH$_2$—C$_6$H$_4$—CH$_2$CO— | H | —N(CH$_3$)$_2$ |
| 47 | dibenzofuranyl-OCH$_2$CH$_2$CO— | H | —N(CH$_3$)$_2$ |
| 48 | [2-(2,4-dichlorophenoxy)phenyl]CH$_2$CO— | H | —N(C$_2$H$_5$)$_2$ |
| 49 | [2,3,4,9-tetrahydro-propyl-pyrano-indolyl]CH$_2$CO— | H | 4-methylpiperazin-1-yl |
| 50 | [3-chloro-4-(pyrrol-1-yl)phenyl]CH(CH$_3$)CO— | H | piperidin-1-yl |

-continued

COMPOUNDS OF FORMULA (I)

| Example Number | R—C(=O)— | R₃ | —N(R₁)(R₂) |
|---|---|---|---|
| 51 | 2,5-diphenylfuran-3-yl-CH₂CH₂CO— | H | —N(C₂H₅)₂ |
| 52 | 2-[(3-chloro-2-methylphenyl)amino]pyridin-3-yl-CO— | H | morpholino |
| 53 | 2-(4'-fluorobiphenyl-3-yl)-propanoyl [CH(CH₃)—CO—] | H | imidazol-1-yl |
| 54 | phenothiazine-type: 2-(trifluoromethyl)phenyl—S—, NH bridge, CO— on other ring | H | —N(C₂H₅)₂ |
| 55 | 1-(4-chlorobenzoyl)-5-methoxy-2-methylindol-3-yl-CH₂CO— (indomethacin) | H | piperidino |
| 56 | 1-(4-chlorobenzoyl)-5-methoxy-2-methylindol-3-yl-CH₂CO— | H | —N(cyclohexyl)₂ |
| 57 | 1-(4-chlorobenzoyl)-5-methoxy-2-methylindol-3-yl-CH₂CO— | H | pyrrolidin-1-yl |

-continued
COMPOUNDS OF FORMULA (I)

| Example Number | R—C(=O)— | R₃ | —N(R₁)(R₂) |
|---|---|---|---|
| 58 | 1-(4-chlorobenzoyl)-5-methoxy-2-methylindol-3-yl-CH₂CO— | H | pyrrol-1-yl |
| 59 | 1-(4-chlorobenzoyl)-5-methoxy-2-methylindol-3-yl-CH₂CO— | H | indol-1-yl |
| 60 | 1-(4-chlorobenzoyl)-5-methoxy-2-methylindol-3-yl-CH₂CO— | H | isoindol-2-yl |
| 61 | 1-(4-chlorobenzoyl)-5-methoxy-2-methylindol-3-yl-CH₂CO— | H | purin-7-yl |
| 62 | 1-(4-chlorobenzoyl)-5-methoxy-2-methylindol-3-yl-CH₂CO— | H | 2,3-dihydropyrrol-1-yl |
| 63 | 1-(4-chlorobenzoyl)-5-methoxy-2-methylindol-3-yl-CH₂CO— | H | 4,5-dihydroimidazol-1-yl |

-continued

COMPOUNDS OF FORMULA (I)

| Example Number | R—C(=O)— | R₃ | —N(R₁)(R₂) |
|---|---|---|---|
| 64 | 6-fluoro-2-methyl-1-[(4-methylsulfinyl)benzylidene]-1H-indene-3-yl-CH₂CO— | H | —N(C₂H₅)₂ |
| 65 | 6-fluoro-2-methyl-1-[(4-methylsulfinyl)benzylidene]-1H-indene-3-yl-CH₂CO— | H | 4-methylpiperazin-1-yl |
| 66 | 2-(acetyloxy)benzoyl— (CH₃COO-C₆H₄-CO—) | H | —N(C₂H₅)₂ |
| 67 | 6-fluoro-2-methyl-1-[(4-methylsulfinyl)benzylidene]-1H-indene-3-yl-CH₂CO— | H | —N(CH₃)₂ |
| 68 | 6-fluoro-2-methyl-1-[(4-methylsulfinyl)benzylidene]-1H-indene-3-yl-CH₂CO— | H | pyrrolidin-1-yl |
| 69 | 1-(4-chlorobenzoyl)-5-methoxy-2-methyl-1H-indol-3-yl-CH₂CO— | —CCl₃ | 4-methylpiperazin-1-yl |

-continued

COMPOUNDS OF FORMULA (I)

| Example Number | $R-\underset{\underset{O}{\|}}{C}-$ | $R_3$ | $-N\underset{R_2}{\overset{R_1}{\diagdown}}$ |
|---|---|---|---|
| 70 | 5-methoxy-2-methyl-1-(4-chlorobenzoyl)indol-3-yl-CH$_2$CO— | $-\underset{\underset{O}{\|}}{C}-CH_3$ | $-N\underset{\diagdown\_\_/}{\diagup\overline{\phantom{xx}}\diagdown}N-CH_3$ |
| 71 | 5-methoxy-2-methyl-1-(4-chlorobenzoyl)indol-3-yl-CH$_2$CO— | $-\underset{\underset{O}{\|}}{C}-C_6H_5$ | $-N\underset{\diagdown\_\_/}{\diagup\overline{\phantom{xx}}\diagdown}N-CH_3$ |
| 72 | 5-methoxy-2-methyl-1-(4-chlorobenzoyl)indol-3-yl-CH$_2$CO— | 2-pyridyl | $-N\underset{\diagdown\_\_/}{\diagup\overline{\phantom{xx}}\diagdown}N-CH_3$ |
| 73 | 5-methoxy-2-methyl-1-(4-chlorobenzoyl)indol-3-yl-CH$_2$CO— | 4-pyridyl | $-N\underset{\diagdown\_\_/}{\diagup\overline{\phantom{xx}}\diagdown}N-CH_3$ |
| 74 | 5-methoxy-2-methyl-1-(4-chlorobenzoyl)indol-3-yl-CH$_2$CO— | 2-furyl | $-N\underset{\diagdown\_\_/}{\diagup\overline{\phantom{xx}}\diagdown}N-CH_3$ |
| 75 | 5-methoxy-2-methyl-1-(4-chlorobenzoyl)indol-3-yl-CH$_2$CO— | H | $-N\underset{(i-C_3H_7)}{\overset{(i-C_3H_7)}{\diagdown}}$ |

The anti-inflammatory activity of the prodrugs of formula (I) is evident from the results of the mouse ear assay [C. G. Van Arman, *Clin. Pharm. Ther.*, 16, 900 (1974)] obtained when representative species of the invention were employed as the test compound. Details of the mouse ear assay are as follows:

The test animal was the male ddY strain mouse (20-25 grams each). Solutions of the test compound in acetone containing 2% croton oil (i.e. a solution containing 98 parts of acetone to 2 parts of croton oil) were prepared for varying concentrations of the test compound. Then, the test animals were anesthetized and 0.05 ml of the selected test solution was applied in 0.025 ml aliquots, one each to the anterior and posterior surface of the right ear of each mouse. Three hours after application, the mice were sacrificed via ether inhalation and both ears were removed from each mouse. Then, one circular section, 8 mm in diameter, was taken from each ear using a leather punch. The increase in weight caused by the irritant was determined by subtracting the weight of the untreated left ear section from that of the right ear section. Drug effects expressed as percent inhibition were determined at each selected concentration (molarity) of each test compound according to the following equation:

$$\% \text{ inhibition} = \frac{\text{Mean Weight Increase control} - \text{Mean Weight Increase for treated}}{\text{Mean Weight Increase for control}} \times 100$$

Groups of 15 mice were treated at each dosage level of each test compound. The control group consisted of 30 mice. In the control group, the right ear of each mouse was treated with the croton oil/acetone solution described above but not containing test compound, while the left ear of each control mouse was untreated.

Indomethacin, indomethacin hydroxamic acid and the compounds of Examples 3, 4 and 5 were tested according to the mouse ear assay described above. The $ED_{50}$, that is, the dosage which was effective in reducing the weight of the ear by 50%, was obtained for each test compound from linear regression analysis of data obtained at $2 \times 10^{-2}$, $4 \times 10^{-2}$ and $8 \times 10^{-2}$ M dosage levels, i.e. the percent inhibition as calculated above was plotted against concentration and the point at which inhibition was 50% was considered the $ED_{50}$ for a given compound. The results were as follows:

| TEST COMPOUND | $ED_{50}$ (M) |
| --- | --- |
| Indomethacin | 0.061 |
| Indomethacin hydroxamic acid | 0.096 |
| α-[1-(4'-Chlorobenzoyl)-5-methoxy-2-methylindol-3-yl]-N—(morpholinomethyl)-acetohydroxamic acid | 0.054 |
| α-[1-(4'-Chlorobenzoyl)-5-methoxy-2-methylindol-3-yl]-N—[(4-methylpiperazin-1-yl)methyl]acetohydroxamic acid | 0.027 |
| α-[1-(4'-Chlorobenzoyl)-5-methoxy-2-methylindol-3-yl]-N—(N',N'—diethylaminomethyl)-acetohydroxamic acid | 0.041 |

The compounds of the present invention are conveniently administered to warm-blooded animals via conventional oral or topical administration, most conveniently by combining the selected compound with any suitable nontoxic pharmaceutically acceptable oral or topical inert carrier material. Such carrier materials are well known to those skilled in the art of oral and topical pharmaceutical formulations. For those not skilled in the art, reference is made to the text entitled, "REMINGTON'S PHARMACEUTICAL SCIENCES" (Fourteenth Edition), 1970. In a typical preparation for oral administration, e.g., tablet or capsule, any one of the compounds of the instant invention is combined in an anti-inflammatory effective amount with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citris pulp, carboxymethylcellulose and sodium lauryl sulfate. If desired, a conventional pharmaceutically acceptable dye can be incorporated into the dosage unit form, i.e., any of the standard FD&C dyes.

Similarly, in a typical formulation for topical application, any one of the compounds of the instant invention is combined with a topical vehicle such as triacetin, such that the active ingredient is present in an anti-inflammatory effective amount. The preparation is simply applied topically to the inflamed area, whereby the therapeutically active compound is dermally absorbed and "cleaved" to release the parent moiety at the site of inflammation.

Naturally, the therapeutic dosage range for the compounds of the instant invention will vary with the size and needs of the patient. However, generally speaking, the following dosage guidelines will suffice. On an oral basis, the therapeutic dose required for a compound of the instant invention will generally, on a molecular basis, mimic that for the parent conventional non-steroidal moiety (e.g., indomethacin, aspirin, naproxen, or the like). On a topical basis, application of an 0.01% to 2.5% concentration of a compound of the instant invention (in a suitable topical carrier material) to the site of inflammation should suffice.

From the foregoing description, one of ordinary skill in the art can easily ascertain the essential characteristics of the instant invention, and without departing from the spirit and scope thereof, can make various changes and/or modifications of the instant invention to adapt it to various usages and conditions. As such, these changes and/or modifications are properly, equitably and intended to be, within the full range of equivalence of the following claims.

What is claimed is:

1. A compound of the formula

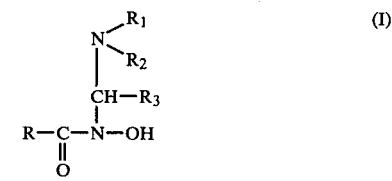

wherein

is the acyl residue of indomethacin; $R_1$ and $R_2$, which can be the same or different, each represent a member selected from the hydrocarbon group consisting of alkyl of 1 to 20 carbon atoms; alkenyl or 2 to 20 carbon atoms;

aryl or 6 to 10 carbon atoms; cycloalkyl of 3 to 8 carbon atoms; cycloalkenyl of 4 to 8 carbon atoms; alkynyl of 2 to 20 carbon atoms; aralkyl, alkaryl, aralkenyl, aralkynyl, alkenylaryl, and alkynylaryl, wherein the alkyl, alkenyl, alkynyl, and aryl portions are defined as above; or $R_1$ and $R_2$ are combined so that $-NR_1R_2$ together represent the residue of a saturated heterocyclic compound containing one secondary nitrogen atom; $R_3$ is hydrogen or $R_1$; or a non-toxic pharmaceutically acceptable acid addition salt or oxide thereof.

2. A compound according to claim 1 wherein at least one of $R_1$ and $R_2$ is alkyl.

3. A compound according to claim 1 wherein at least one of $R_1$ and $R_2$ is $C_1-C_8$ alkyl.

4. A compound according to claim 1 wherein $R_1$ and $R_2$ are each alkyl.

5. A compound according to claim 1 wherein $R_1$ and $R_2$ are each $C_1-C_8$ alkyl.

6. A compound according to claim 1 wherein at least one of $R_1$ and $R_2$ is alkenyl.

7. A compound according to claim 1 wherein at least one of $R_1$ and $R_2$ is $C_2-C_8$ alkenyl.

8. A compound according to claim 1 wherein at least one of $R_1$ and $R_2$ is aryl.

9. A compound according to claim 1 wherein at least one of $R_1$ and $R_2$ is cycloalkyl.

10. A compound according to claim 1 wherein at least one of $R_1$ and $R_2$ is $C_5-C_6$ cycloalkyl.

11. A compound according to claim 1 wherein at least one of $R_1$ and $R_2$ is cycloalkenyl.

12. A compound according to claim 1 wherein at least one of $R_1$ and $R_2$ is $C_5-C_6$ cycloalkenyl.

13. A compound according to claim 1 wherein at least one of $R_1$ and $R_2$ is alkynyl.

14. A compound according to claim 1 wherein at least one of $R_1$ and $R_2$ is $C_2-C_8$ alkynyl.

15. A compound according to claim 1 wherein at least one of $R_1$ and $R_2$ is aralkyl.

16. A compound according to claim 15 wherein the alkyl portion of the aralkyl radical contains 1 to 6 carbon atoms.

17. A compound according to claim 1 wherein at least one of $R_1$ and $R_2$ is alkaryl.

18. A compound according to claim 1 wherein at least one of $R_1$ and $R_2$ is aralkenyl.

19. A compound according to claim 1 wherein at least one of $R_1$ and $R_2$ is aralkynyl.

20. A compound according to claim 1 wherein at least one of $R_1$ and $R_2$ is alkenylaryl.

21. A compound according to claim 1 wherein at least one of $R_1$ and $R_2$ is alkynylaryl.

22. A compound according to claim 1 wherein $R_1$ and $R_2$ are combined so that $-NR_1R_2$ together represent the residue of a saturated heterocyclic compound containing one secondary nitrogen atom.

23. A compound according to claim 22 wherein the residue is that of a saturated monocycle containing one or more hetero atoms in the ring and optionally bearing one or more phenyl, benzyl or methyl substituents.

24. A compound according to claim 23 wherein the residue is selected from the group consisting of morpholino, 1-pyrrolidinyl, 4-benzyl-1-piperazinyl, 4-methyl-1-piperazinyl, piperidino, hexamethyleneimino, 4-phenylpiperidino, 2-methyl-1-pyrazolidinyl, 3-methyl-1-imidazolidinyl, 4-benzylpiperidino and 4-phenyl-1-piperazinyl.

25. A compound according to claim 1 wherein $R_3$ is hydrogen.

26. A compound according to claim 1 wherein $R_3$ is $R_1$.

27. A compound according to claim 26 wherein $R_1$ is an alkyl radical.

28. The compound according to claim 1 which is α-[1-(4'-chlorobenzoyl)-5-methoxy-2-methylindol-3-yl]-N-(morpholinomethyl)acetohydroxamic acid.

29. The compound according to claim 1 which is α-[1-(4'-chlorobenzoyl)-5-methoxy-2-methylindol-3-yl]-N-(N',N'-diethylaminomethyl)acetohydroxamic acid.

30. The compound according to claim 1 which is α-[1-(4'-chlorobenzoyl)-5-methoxy-2-methylindol-3-yl]-N-[(4-methylpiperazin-1-yl)methyl]acetohydroxamic acid.

31. The compound according to claim 1 which is selected from the group consisting of:

α-[1-(4'-chlorobenzoyl)-5-methoxy-2-methylindol-3-yl]-N-(piperidinomethyl)acetohydroxamic acid;

α-[1-(4'-chlorobenzoyl)-5-methoxy-2-methylindol-3-yl]-N-[(pyrrolidin-1-yl)methyl]acetohydroxamic acid;

α-[1-(4'-chlorobenzoyl)-5-methoxy-2-methylindol-3-yl]-N-(N',N'-dicyclohexylaminomethyl)acetohydroxamic acid;

α-[1-(4'-chlorobenzoyl)-5-methoxy-2-methylindol-3-yl]-N-(N',N'-dimethylaminomethyl)acetohydroxamic acid;

α-[1-(4'-chlorobenzoyl)-5-methoxy-2-methylindol-3-yl]-N-(N',N'-diisopropylaminomethyl)acetohydroxamic acid;

α-[1-(4'-chlorobenzoyl)-5-methoxy-2-methylindol-3-yl]-N-(N',N'-dipentylaminomethyl)acetohydroxamic acid; and α-[1-(4'-chlorobenzoyl)-5-methoxy-2-methylindol-3-yl]-N-(N',N'-dioctylaminomethyl)acetohydroxamic acid.

32. A pharmaceutical composition of matter comprising an anti-inflammatory effective amount of a compound of claim 1, in combination with a nontoxic pharmaceutically acceptable inert carrier therefor.

33. A method for alleviating inflammation in or on a warm-blooded animal exhibiting an inflammatory response, which comprises administering thereto an anti-inflammatory effective amount of a compound as claimed in claim 1.

34. A method for alleviating inflammation in or on a warm-blooded animal exhibiting an inflammatory response, which comprises administering thereto an anti-inflammatory effective amount of a composition as claimed in claim 32.

* * * * *